United States Patent [19]

Sato et al.

[11] Patent Number: 5,017,787
[45] Date of Patent: May 21, 1991

[54] DESK TOP TYPE INFRARED RADIATION MOISTURE MEASURING APPARATUS

[75] Inventors: Kiyomi Sato; Yasuo Saito, both of Kanagawa, Japan

[73] Assignee: Japan Tobacco, Inc., Japan

[21] Appl. No.: 429,583

[22] Filed: Oct. 31, 1989

[30] Foreign Application Priority Data

Nov. 4, 1988 [JP] Japan .................. 63-143422[U]

[51] Int. Cl.$^5$ ...................... G01N 21/01; G01N 21/35
[52] U.S. Cl. .................. 250/360.1; 250/339; 250/341
[58] Field of Search ............ 250/360.1, 341, 339

[56] References Cited

U.S. PATENT DOCUMENTS 4,823,009  4/1989  Biemann et al. .................. 250/341

FOREIGN PATENT DOCUMENTS 58-7547  1/1983  Japan .................. 356/436

OTHER PUBLICATIONS

J. J. Kubik, "Rotation of Micro Samples for Infrared Spectrophotometer Analysis", *Western Electric Technical Digest*, No. 3 (Jul. 1966), pp. 21-22.

*Primary Examiner*—Constantine Hannaher
*Attorney, Agent, or Firm*—Lowe, Price, LeBlanc, Becker & Shur

[57] ABSTRACT

A desk-top type infrared radiation moisture measuring apparatus is of a type in which the moisture in a specimen is exposed to a measurement light easily absorbed into water and to at least one reference light not noticeably absorbed into water and calculation is performed to determine the moisture in the specimen on the basis of both the measurement light and the reference light, reflected from the specimen. The apparatus comprises a turntable on which the specimen is placed and which is exposed to both the measurement light and the reference light from above at a portion away from the center thereof, and a drive source for driving the turntable into rotation. The measurement is carried out while the turntable is being rotated.

2 Claims, 7 Drawing Sheets

DESK TOP TYPE INFRARED RADIATION MOISTURE MEASURING APPARATUS

BACKGROUND OF THE INVENTION

1. Field of the Invention

The present invention relates to an apparatus for measuring moisture within a specimen by exposing near-infrared radiation thereto, and more particularly to a compact desk-top type infrared radiation moisture measuring apparatus in which unusually large errors due to variations in the amount of lights reflected from a specimen may be eliminated.

2. Prior Art

Conventionally, a so-called infrared radiation moisture meter has been known as an apparatus for measuring moisture by use of near-infrared radiation where a measurement light in the near-infrared radiation region that is easily absorbed by water is exposed to the specimen, and the moisture within the specimen is measured on the basis of the light reflected from the specimen. With this type of moisture meter, a reference light that is not absorbed by water appreciably is exposed to the specimen just as is in the measurement light, and the amounts of the reflected measurement light is compared with that of the reflected reference light to compensate for measurement errors due to difference in the colors or compounds of the specimen.

This type of moisture measuring apparatus finds its application in determining moisture rate within tobacco leaves being carried on the conveyor of a tobacco manufacturing process for controlling moisture content in the tobacco leaves. A compact desk-top type infrared radiation moisture measuring apparatus that operates on the above-mentioned principle has been proposed for facilitating measurement of the moisture in various specimens in a laboratory.

However, unlike drying method, this type of apparatus indirectly measures the moisture in terms of the amount of the reflected lights exposed to the specimen; therefore the apparatus suffers from a problem that variations of the moisture depending on light-exposed portions or the top shape of the specimen, e.g., the surface shape of powder-like specimens, is a source of measurement errors. This measurement error causes little or no effect in controlling the moisture in a large quantity of the tobacco leaves, for example, in the tobacco manufacturing process but is a serious problem in measuring the moisture of a specimen of a small quantity, such as measurement of moisture using the desk-top infrared radiation moisture measuring apparatus where the moisture in a small amount of specimen is determined through a limited number of measurements.

SUMMARY OF THE INVENTION

An object of the present invention is to allow every portion of the surface of the specimen to be equally exposed to a light so that an operator can effectively make a large number of measurements in succession for obtaining an average value of the amount of lights reflected from the specimen to eliminate unusually larger errors that may possibly be introduced into the moisture measurement in the specimen.

A desk-top type infrared radiation moisture measuring apparatus according to the present invention is of a type in which both a measurement light that is easily absorbed into water and at least one reference light not significantly absorbed into water are exposed to a specimen and the moisture measurement is carried out on the basis of both the measurement light and reference light reflected back by the specimen. The apparatus comprises a turntable on which the specimen is placed and which is exposed to both the measurement light and the reference light from above at a portion away from the rotational center thereof, and a drive means for driving the turntable into rotation. The specimen placed on the turntable is measured the moisture contained therein while the turntable is being rotated.

BRIEF DESCRIPTION OF THE DRAWINGS

Features and other objects of the invention will be more apparent from the description of preferred embodiments and the accompanying drawings in which.

DETAILED DESCRIPTION OF PREFERRED EMBODIMENTS

Operation

A turntable on which a specimen is placed is rotated by a rotative drive means. A measurement light is exposed to the specimen alternately with a reference light. The lights are exposed to a portion away from the center of rotation of the turntable so that when the turntable carrying the specimen thereon is rotated, every portion of the specimen is exposed to the lights in turn. The measurement light is reflected from the specimen while also being absorbed by a large amount into the moisture within the specimen. The reference light is also reflected from the specimen but is not appreciably absorbed into the moisture within the specimen. These reflected lights are converted into voltage signals indicative of the amount of the reflected lights. The voltage signals are obtained periodically, and the voltage signals associated with the measurement light and those associated with the reference light are averaged, respectively over a predetermined time interval while the turntable is being rotated.

Figure 6:
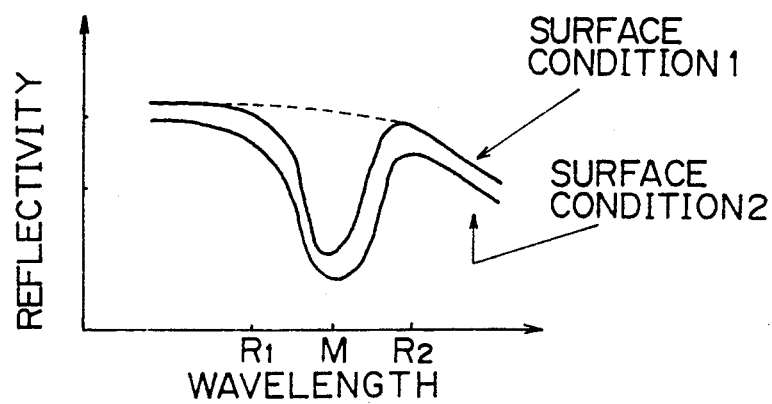
FIG. 6 shows two different curves of reflectivity for a given specimen, depending on the surface condition of the specimen.

It should be noted that the reflectivity is not always constant for a given specimen but varies by a relatively large amount depending on the surface condition of the specimen. This can be seen from FIG. 6, where two different curves of reflectivity are shown for a given same specimen depending on the surface condition thereof. In FIG. 6, R1, R2, and M are the first reference light, the second reference light, and the measurement light, respectively. The two curves in FIG. 6 imply that the measurement of the lights from the specimen will include an error due to the amount of reflected lights, which is dependent on the surface condition of the specimen. This error is eliminated by taking the difference in absorbance ($x = \ln R/M$) between the measurement light and the reference light. THis is why both the measurement light and the reference lights are used. Most of the specimens exhibit a tendency of inclined base line (dotted line in FIG. 6) as is seen from FIG. 6; therefore two reference lights are provided on both sides of the measurement light in an equally spaced apart relation relative to the measurement light. The average of the amount of two reflected reference lights is used as the reference output which is manipulated together with the reflected measurement light using an equation:

$$x = \ln (\textit{average of reference lights/measurement light})$$

where x is absorbance of the specimen.

Thereby the correct difference in absorbance can be read from the inclined base line to improve accuracy of the moisture measuring apparatus.

By this arrangement, every portion of the surface of the specimen can be equally exposed to the lights when the turn table 4 is rotated, allowing an operator to effectively make a large number of measurements successively. The variations in the amount of lights reflected from the specimen depending on the portion exposed is averaged, thereby preventing one from measuring the moisture in the specimen with unusually large errors.

EXAMPLE

Figure 1:
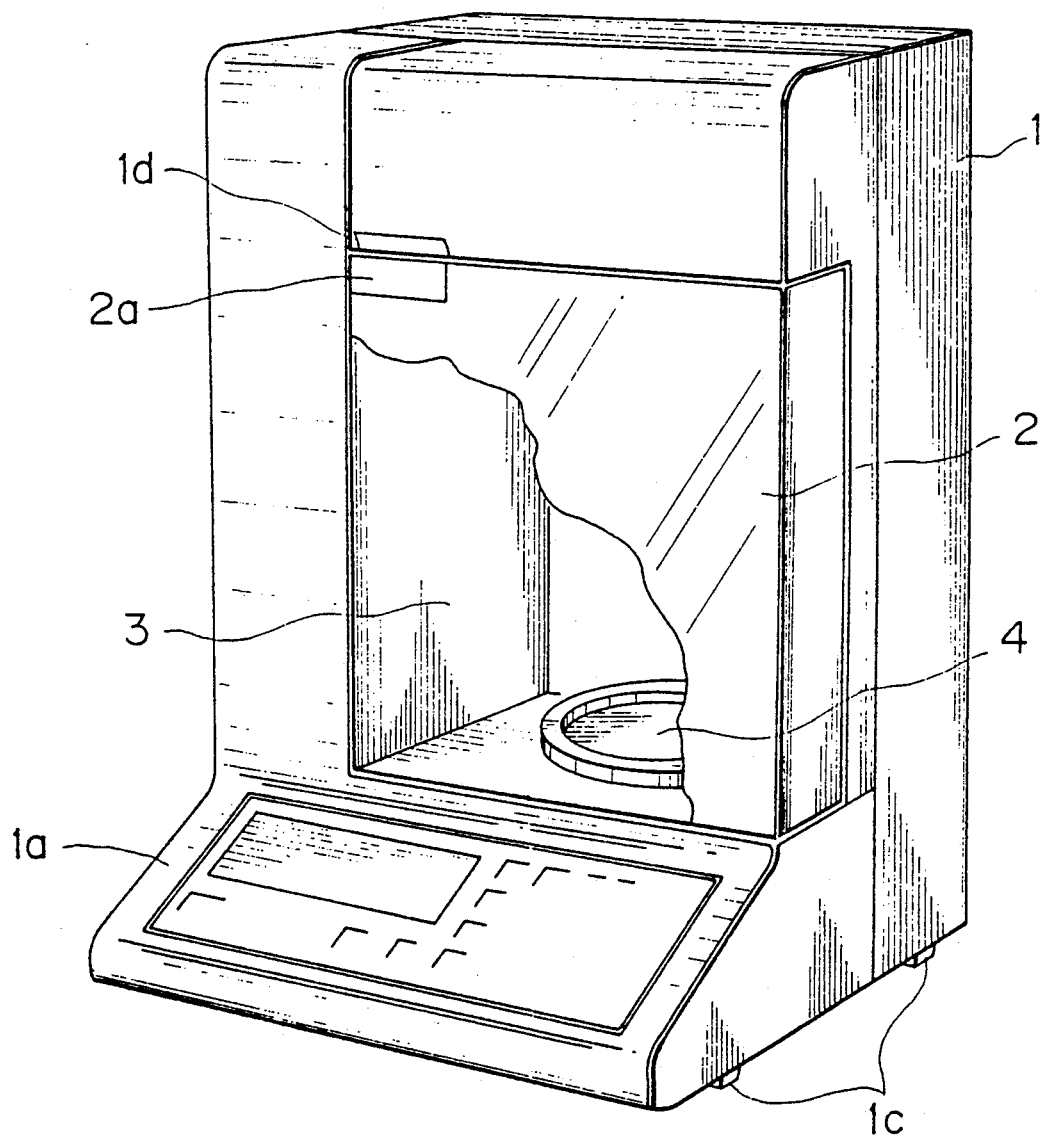
FIG. 1 is partly broken perspective view of a desk-top type infrared radiation moisture measuring apparatus according to the present invention.
Figure 2:
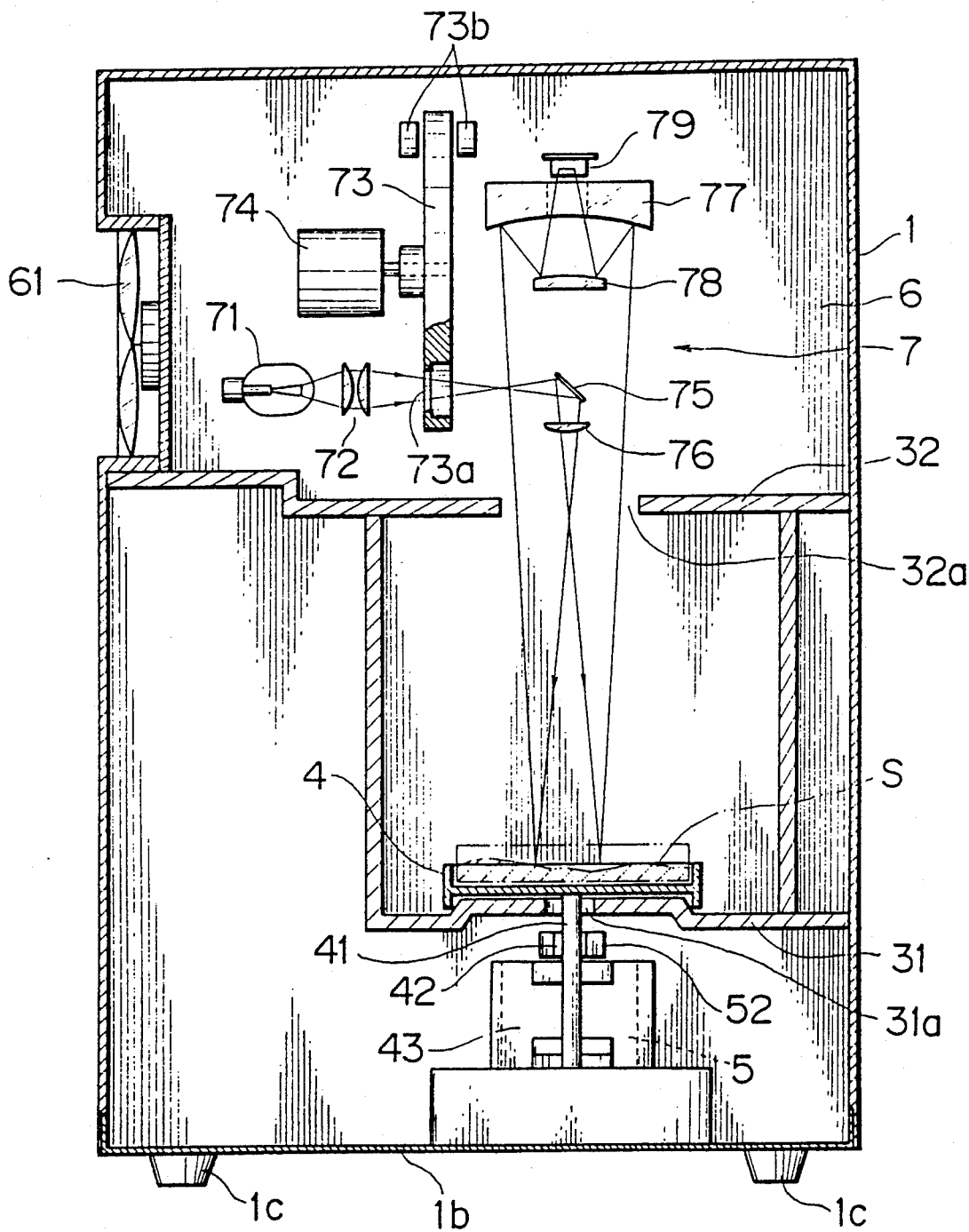
FIG. 2 is a cross-sectional front view of FIG. 1.
Figure 3:
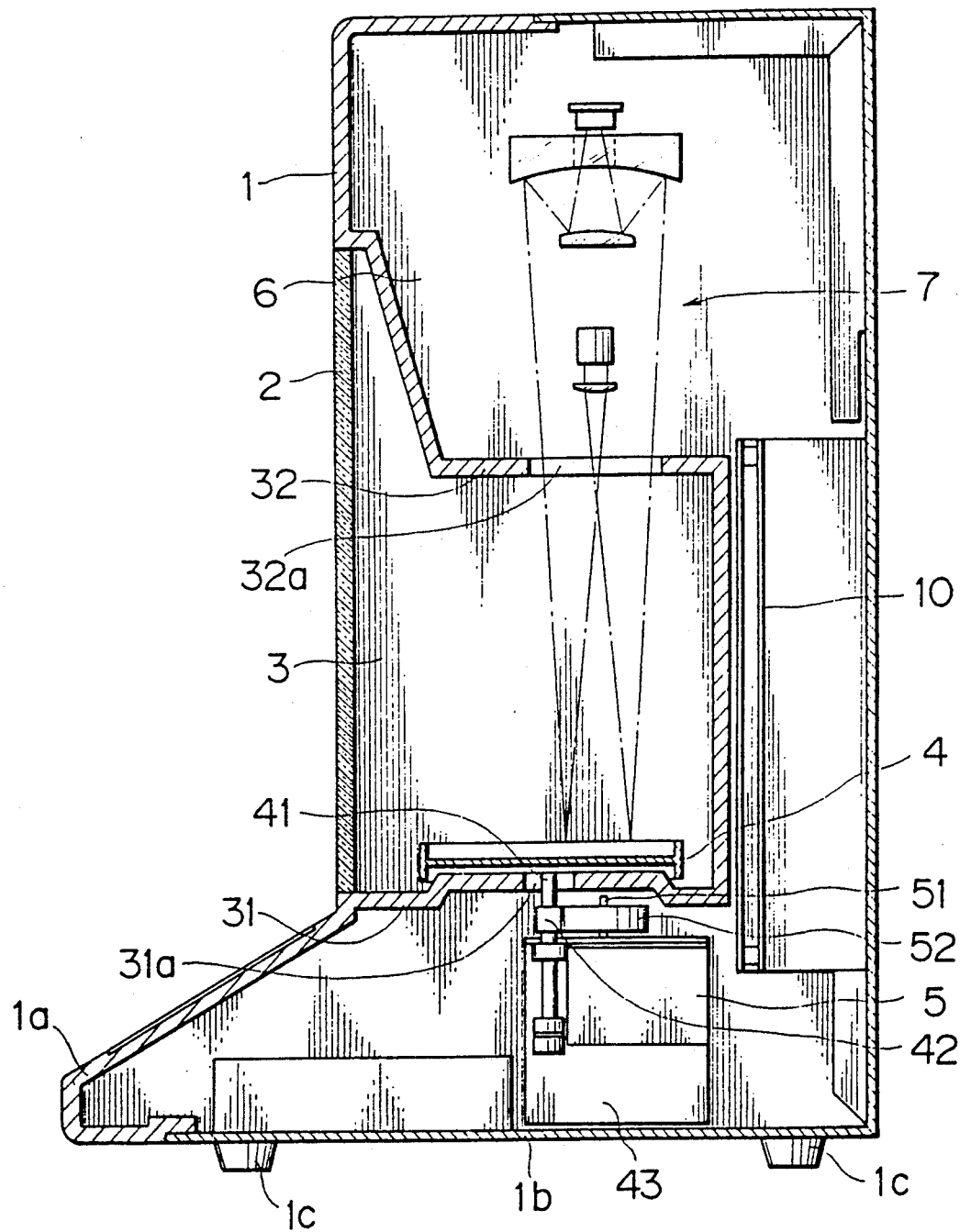
FIG. 3 is a cross-sectional side view of FIG. 1.

FIG. 1 is a partly broken perspective view of a desktop type infrared radiation moisture measuring apparatus according to the present invention, FIG. 2 is a cross-sectional front view of FIG. 1, and FIG. 3 is a cross-sectional side view of FIG. 1.

Referring to FIGS. 1 and 2, a housing 1 is provided with a gray acrylic resin door 2 at the front side thereof. Behind the door 2 is formed a measurement chamber 3 for accommodating a specimen to be measured. Below and at the front side of the chamber 3 is provided an operation/display panel 1a on which operation keys for operating the apparatus and a displayer for indicating the moisture measured. At the four corners of the apparatus are provided rubber feet 1c.

The acrylic resin door 2 is mounted at one side thereof to the side of the housing 1 by means of hinges not shown, and is provided with a door securing plate 2a made of iron at upper corner remote from the hinged side. Behind the door securing plate 2a is mounted a magnet not shown to the housing 1 to which the plate 2a is attracted when the door 2 is closed. A recess 1d is provided in the housing 1 near the plate 2a so that the door 2 can be pulled at the plate 2a.

At the bottom of the chamber 3 is disposed a disk-like turntable 4 having a circular rim at its periphery to form a shallow container. The turntable 4 is made of aluminum and the surface thereof is anodized.

On the underside of the turntable 4 is mounted at the center thereof a rotating shaft 41 extending downwardly through a hole 31a formed in the bottom 31 of the chamber 3. The rotating shaft 41 is journaled by a bearing 43 secured to the bottom plate 1b of the apparatus. To the bearing 43 is mounted a turntable-driving motor 5 to which a spur gear 52 is mounted. The spur gear 52 is in mesh engagement with a spur gear 42 mounted to the rotating shaft 41. When the motor 5 runs, the turntable 4 is driven into rotation through the spur gears 52,42 and the rotating shaft 41.

Above the chamber 3, a ceiling 32 forms an optical system accommodation 6 within which an optical system 7 is accommodated for providing the beam of the measurement light and the reference light as well as for detecting the lights reflected from the specimen. In the middle of the ceiling 32 is formed a window 32a through which the light reflected from or to the specimen S passes.

As shown in FIG. 2, the optical system 7 includes a light source 71, a first condenser lens 72, a rotary disk 73, a disk-driving motor 74, a reflector 75, a second condenser lens 76, a concave mirror 77, a convex mirror 78, and an infrared radiation detector 79.

Figure 4:
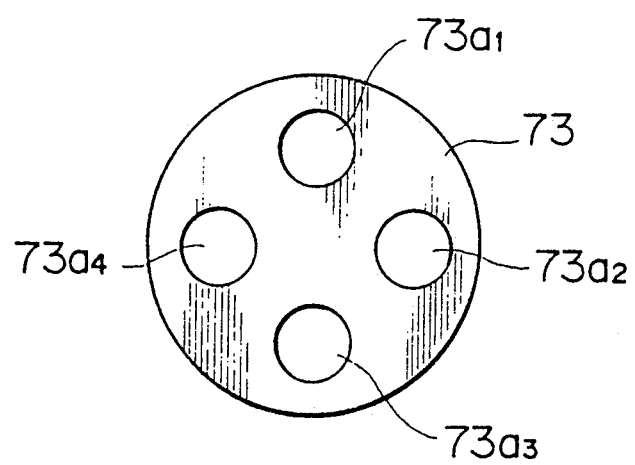
FIG. 4 shows a rotary disk according to the present invention.

As shown in FIG. 4, to the rotary disk 73 are mounted on the same circumference a measurement light interference filter 73a1 through which a measurement light in the near-infrared radiation region is passed to the reflector 75, reference light interference filters 73a2,73a3 for selectively passing two different lights in the near-infrared radiation region as a first reference light and a second reference light, and a visible light interference filter 73a4 for passing a visible light. The measurement light is alight that varies the degree of being absorbed depending on the moisture in the specimen while the first and second reference lights are lights that are not noticeably absorbed into the moisture in the specimens but are reflected from the specimen. The visible light is used for the operator to visually confirm the portion of the specimen where the exposure is supposed to be performed. When the rotary disk 73 is driven into rotation by the disk driving motor 74, the respective filters 73a1-73a4 traverse sequentially an optical path between the first condenser lens 72 and the reflector 75.

In the proximity of the rotary disk 73 is disposed a rotational position detector 73b for detecting the rotational position of the rotary disk 73 by means of, for example, light sensor. The filter which arrives at the above mentioned optical path is identified by detecting the rotational position, i.e., whether the light through a filter is the measurement light or the reference light is determined by an analog processor in a latter described measuring circuit.

The light from the light source 71 is converged by the first condenser lens 72 to subsequently be converted either into the measurement light or into the reference light by the filters 73a1-73a4 of the rotary disk 73a, and is then exposed to the specimen S on the turntable 4 through the reflector 75 and the second condenser lens 76. The light reflected from the specimen S is condensed by the concave mirror 77, is then directed through the convex mirror 78 to the infrared detector 79 which in turn provides a voltage signal having a voltage indicative of the amount of light received to the measuring circuit incorporated in the printed circuit board 10 (FIG. 3).

It should be noted that the beam of light from the second condenser lens 76 is aimed at a portion away from the center of the turntable 4 as depicted in FIG. 3. By this arrangement, every portion of the surface of the specimen can be equally exposed in turn to the lights when the turntable 4 is rotated, allowing an operator to effectively make a large number of measurements successively. The optical system accommodating room 6 in which the optical system 7 is accommodated is of a dark room by which lights emitted in other directions than to the front condenser lens 72 are blocked. On the side of the optical system accommodating room 6 is mounted a cooling fan 61 for exhausting air to the outside, thereby preventing the temperature rise in the room 6 due to the heat generated by the light source 71.

Figure 5:
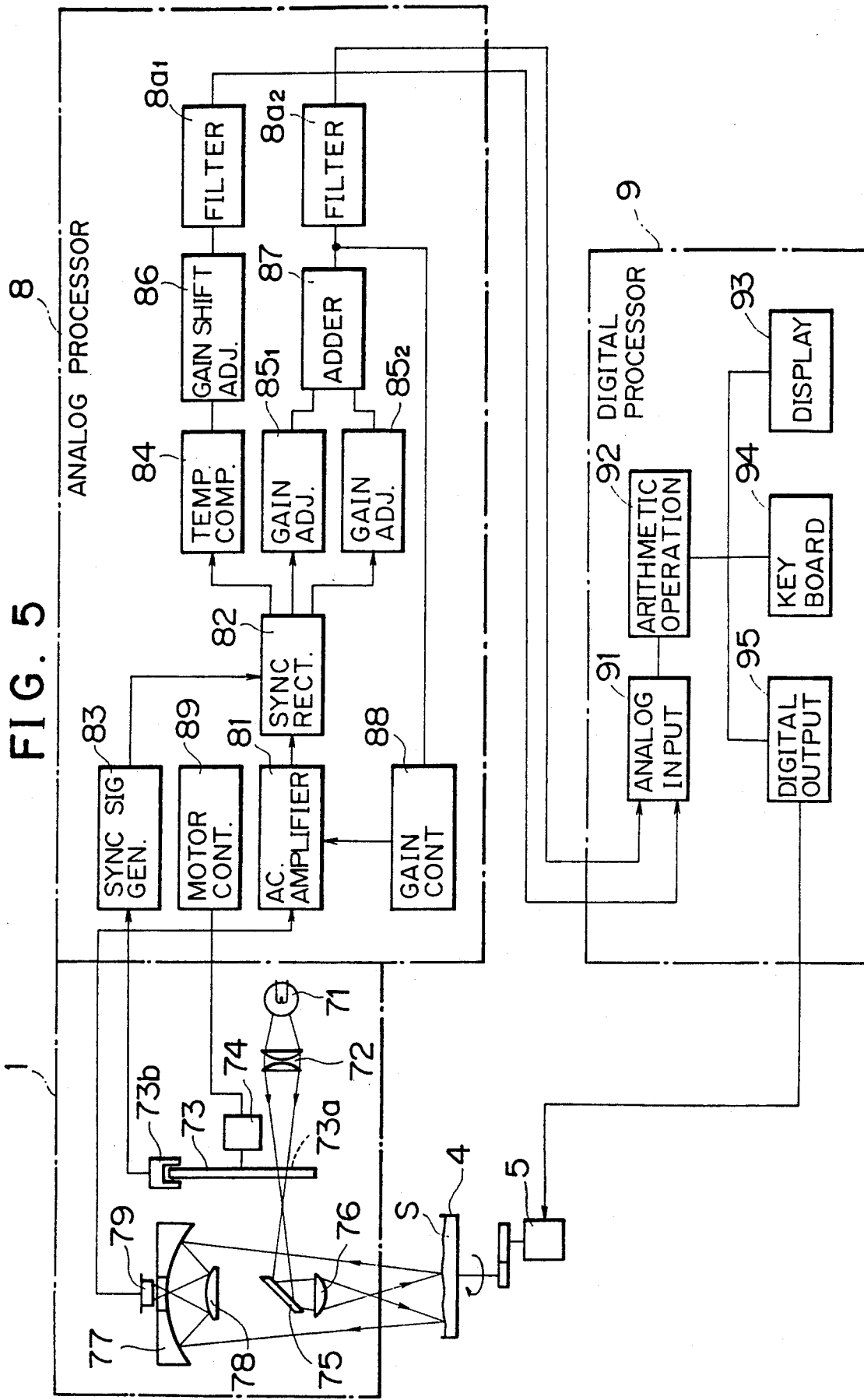
FIG. 5 is a block diagram for showing the present invention.

FIG. 5 is a block diagram for showing an embodiment. A voltage signal from the infrared radiation detector 79 of the optical system 7 is inputted into an analog processing unit 8 in which the voltage signal associated with the measurement light is separated from the voltage signal associated with the reference light while also being filtered, as will be described later. The analog-processed signals are directed to a digital processing unit 9 which performs calculations of the moisture in the specimen and displays the calculated results.

Figure 7A:
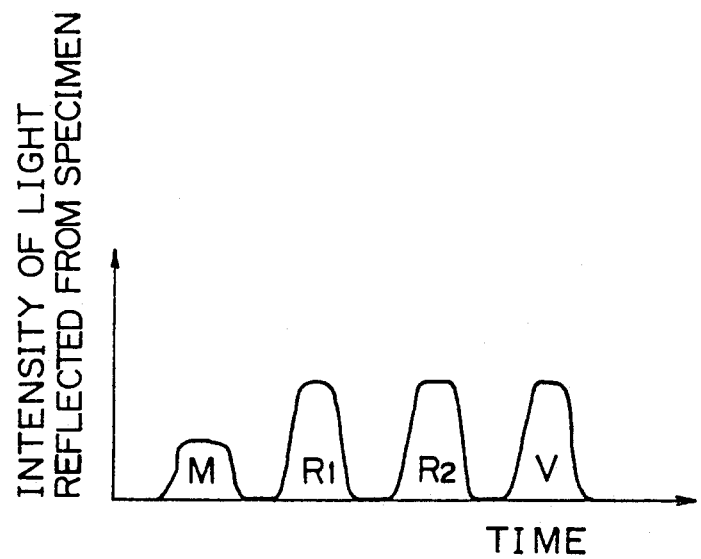
FIGS. 7A-7B show waveforms of the intensity of light reflected from the specimen and output voltage of an infrared radiation detector, respectively.
Figure 7B:
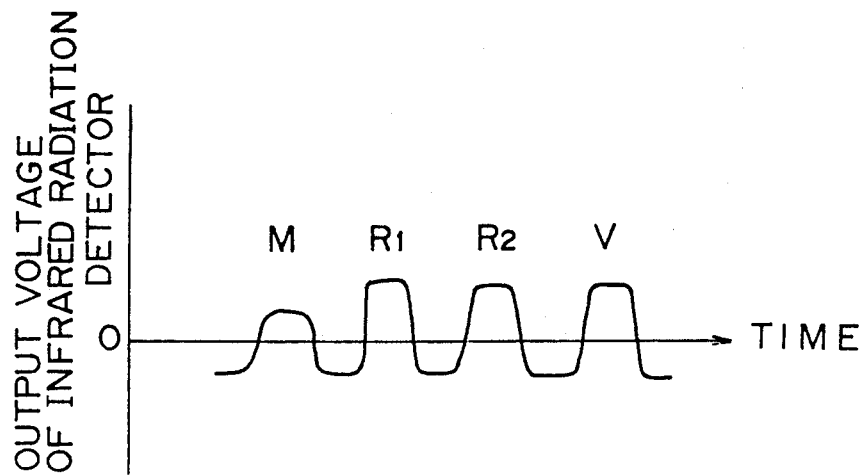

The voltage signal from the infrared radiation detector 79 is of a square wave as shown in FIG. 7B.

This is because the light incident upon the specimen is chopped by a rotary disk 73; therefore the reflected lights from the specimen are also of a square wave as shown in FIG. 7A. In FIGS. 7A–7B, M, R1, R2, and V are the measurement light, the first and second references, and the visual light, respectively. The square wave voltage signal is amplified by an ac amplifier 81 to be fed to a synchronous rectifier 82. A position detection signal from the rotational position detector 73b is inputted into a synchronous signal generator 83 which provides a synchronization signal in accordance with the types of the filter that traverses the optical path in the optical system 7 to the synchronous rectifier 82.

The synchronous rectifier 82 selectively outputs in accordance with the types of the filter 73a in synchronism with the aforementioned synchronization signal the voltage signals received from the am amplifier 81. The voltage signal associated with the measurement light is then outputted to a temperature compensator 84 and the voltage signal associated with the first and second reference lights to gain adjusters 85-1, 85-2, respectively. The temperature compensator 84 functions to compensate the variations in measurements due to varying room temperature.

The voltage signal associated with the measurement light is outputted from the temperature compensator 84 to a filter 8a-1 through a gain shift adjuster 86. The voltage signals associated with the first and second reference lights are inputted into an adder 87 from the gain adjusters 85-1, 85-2, respectively. The output levels from the gain adjusters 85-1, 85-2 are added together to be outputted to a filter 8a-2. The output of the adder 87 is actually the average of the first and second reference lights.

The reflective index of the specimen ranges from less than 10% of black soil to as high as 80% of aluminum. Thus the intensity of lights incident upon the infrared radiation detector 79 varies by a factor of nearly 10. A gain control 88, which receives the outputs of the gain adjusters 85-1, 85-2, the gain shift adjuster 86, and the adder 87, is provided for adjusting the output level of the analog processing unit 8 relative to the amount of moisture measured to thereby allow the apparatus to display the moisture of a given specimen with convenient magnitudes of voltage. That is, the gain control 88 controls the amplification factor of the ac amplifier 81 so that the output of the adder 87 is a constant value. A motor controller 89 is provided for controlling the rotation of the disk driving motor 74 in the optical system 7.

The respective voltage signals associated with the measurement light and the reference light are subjected to filtering through the filters 8a-1, 8a-2, such as a low pass filter which output to the digital processing unit 9 voltage signals averaged out with a predetermined time constant over a predetermined time period. The predetermined time constant is set in accordance with the time required for the rotary disk 73 to make one rotation, that is, both the respective time interval and repetition rate at which the measurement light or the reference light is exposed to the specimen S.

The digital processing unit 9 includes an analog input port 91 provided with primarily an A/D convertor therein, an arithmetic operation processor 92 for processing digital data by, for example, a microprocessor, a keyboard input port such as an operation keys, and a digital output port 95 for outputting signals to be used for controlling the turntable driving motor 5.

The voltages signals associated with the measurement light and the reference light outputted from the analog processing unit 8 are each converted into a digital signal indicative of the level of the voltage by an analog input port 91, subsequently the amount of moisture in the specimen is calculated on the basis of the digital data and is displayed on a displayer 93.

Figure 8:
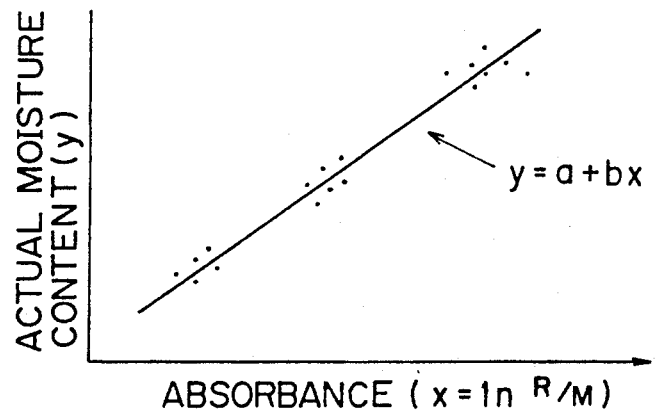
FIG. 8 illustrates a calibration line for a given specimen.

The arithmetic operation processor 92 receives a data M associated with the measurement light from the analog input port 91 and a data R associated with the reference light to perform calculation of absorbance using Eq.(1), from which the amount of moisture y is calculated using Eq.(2).

$$x = \ln(R/M) \quad (1)$$

$$y = a + bx \quad (2)$$

where a and b are conversion coefficients that are precalculated on the basis of the parameter specific to the specimen to be measured and y is in weight percents. For a given material, a large number of specimens having different moisture contents are measured to obtain absorbance ($x = \ln R/M$) for each one of the specimens. The actual moisture content of the respective specimen is measured through the use of a predetermined method such as dry technique or Karl Fischer technique. Then a calibration line ($y = a + bx$) as shown in FIG. 8 is obtained on the basis of each value of absorbance and the corresponding actual moisture content. Thus "a" and "b" are the conversion coefficients for this calibration line.

Some specimen may not be represented by a linear equation such as Eq.(2), in which case the following cubic equation may be used:

$$y = a_0 + a_1 x + a_2 x^2 + a_3 x^3 \quad (3)$$

While, in the aforementioned embodiment, the filters 8a-1, 8a-2 are used for filtering the respective voltage signals to average out the variations both in the measurement light reflected from the specimen and in the reference light reflected from the specimen, the moisture measurements y may be averaged out by a digital filter or the like with a predetermined time constant over each of predetermined time periods.

What is claimed is:

1. A desk-top type infrared radiation moisture measuring apparatus, in which a specimen containing moisture therein is exposed to a measurement light easily absorbed into water and to at least one reference light easily absorbed into water and to measure said moisture on the basis of said measurement light and said reference light reflected from said specimen, comprising:

a turntable on which said specimen is placed and which is exposed to both said measurement light and said reference light from above at a portion away from the rotational center thereof; and a drive means for driving said turntable into rotation;

said specimen placed on said turntable being measured the moisture contained therein while said turntable is being rotated, wherein said reference light includes a first reference light and a second reference light, said first reference light having a wavelength longer than said measurement and said second reference light having a wavelength shorter than said measurement light, and wherein said measurement light reflected from said specimen and reference light reflected from said specimen are each averaged with a predetermined time constant over a predetermined time interval while said turntable is rotated.

2. A desk-top type infrared radiation moisture measuring apparatus in which a specimen containing an amount of moisture therein is exposed to a measuring light, a first reference light having a longer wavelength than the measuring light, and a second reference light having a shorter wavelength than the measuring light in an alternating fashion, and the specimen reflects the reference and measuring lights while absorbing some of the measuring light such that an absorbed amount of the measuring light depends on the amount of moisture contained in the specimen comprising:

a turntable on which the specimen is placed and onto which the measurement and reference lights are exposed, said turntable defining a circular sample track of the specimen when said turntable is rotated; and drive means for driving said turntable into rotation; and signal processing means for receiving the reflected measuring and reference lights along the circular sample track when the turntable is rotated and for averaging the amounts of the received measuring and reference lights with a predetermined time constant over a predetermined time length so as to determine the amount of moisture contained in the specimen on the basis of the averaged amounts of received measuring and reference lights.

* * * * *